(12) United States Patent
Boudaoud et al.

(10) Patent No.: US 8,482,298 B2
(45) Date of Patent: Jul. 9, 2013

(54) LIQUID LEVEL AND COMPOSITION SENSING SYSTEMS AND METHODS USING EMF WAVE PROPAGATION

(75) Inventors: Idir Boudaoud, Antibes (FR); Alan Kenneth McCall, Antrim (GB); Adrian M. Page, Antrim (GB)

(73) Assignee: Schrader Electronics Ltd., Antrim (GB)

( * ) Notice: Subject to any disclaimer, the term of this patent is extended or adjusted under 35 U.S.C. 154(b) by 289 days.

(21) Appl. No.: 11/800,965

(22) Filed: May 8, 2007

(65) Prior Publication Data

US 2008/0143345 A1    Jun. 19, 2008

Related U.S. Application Data

(60) Provisional application No. 60/875,439, filed on Dec. 18, 2006.

(51) Int. Cl.
*G01R 27/32* (2006.01)
*G01N 11/00* (2006.01)
*G01N 21/00* (2006.01)

(52) U.S. Cl.
USPC .......... 324/652; 324/644; 73/53.01; 73/24.02

(58) Field of Classification Search
USPC ............ 324/652, 654, 601, 644; 73/290–334, 73/53.01, 1.06, 24.02
See application file for complete search history.

(56) References Cited

U.S. PATENT DOCUMENTS

| 2,720,624 | A | | 9/1951 | Gunst, et al. ................... 324/61 |
|---|---|---|---|---|
| 2,772,393 | A | | 11/1956 | Davis .............................. 314/40 |
| 3,256,482 | A | | 6/1966 | Rosso ............................. 324/61 |
| 3,540,275 | A | * | 11/1970 | Post et al. .................... 73/290 V |
| 4,599,892 | A | * | 7/1986 | Doshi ............................ 73/49.2 |
| 4,651,105 | A | * | 3/1987 | Inbar .............................. 327/58 |
| 4,729,245 | A | * | 3/1988 | Hansman, Jr. .................. 73/865 |
| 4,769,593 | A | | 9/1988 | Reed et al. .................. 324/61 R |
| 5,088,325 | A | * | 2/1992 | Eichberger et al. ......... 73/304 C |
| 5,150,683 | A | | 9/1992 | Depa et al. ................... 123/417 |

(Continued)

FOREIGN PATENT DOCUMENTS

WO    WO 2006/122173 A2    11/2006
WO    WO 2008/076453 A1    6/2008

OTHER PUBLICATIONS

Notification of Transmittal of the International Search Report and the Written Opinion of the International Searching Authority, or the Declaration International Application No. PCT/IB2008/003071, Date of Mailing Apr. 15, 2009.

*Primary Examiner* — Melissa Koval
*Assistant Examiner* — Farhana Hoque
(74) *Attorney, Agent, or Firm* — Holland & Hart LLP

(57) ABSTRACT

An automotive urea solution monitoring device is deployed in conjunction with the urea tank of a selective catalytic reduction vehicle. An RF signal of a constant frequency may be generated across a resonant circuit, which may be comprised of an inductor and a PCB trace capacitor, or the like. Electromagnetic radiation is propagated into the automotive urea solution in the urea tank. The conductivity and dielectric properties of the liquid change the impedance of the discrete/trace capacitor and or the discrete/trace inductor. These changes are proportional to ammonia content, temperature, and/or level of the automotive urea solution in the urea tank and are preferably detected by a microcontroller, or the like, and then transmitted to a selective catalytic reduction vehicle engine management system, or the like.

19 Claims, 4 Drawing Sheets

U.S. PATENT DOCUMENTS

| | | | |
|---|---|---|---|
| 5,301,542 A | 4/1994 | Meitzler et al. | 73/61 |
| 5,414,368 A | 5/1995 | Ogawa et al. | 324/675 |
| 5,440,310 A | 8/1995 | Schreiner | 342/124 |
| 5,497,753 A | 3/1996 | Kopera | 123/494 |
| 5,832,772 A | 11/1998 | McEwan | 73/290 R |
| 6,018,247 A * | 1/2000 | Kelly | 324/644 |
| 6,078,280 A | 6/2000 | Perdue et al. | 342/124 |
| 6,293,142 B1 | 9/2001 | Pchelnikov et al. | 73/290 R |
| 6,505,509 B2 * | 1/2003 | Gualtieri | 73/290 V |
| 6,564,658 B2 * | 5/2003 | Pchelnikov et al. | 73/866 |
| 7,276,916 B2 | 10/2007 | Hammer | 324/634 |
| 7,319,401 B2 | 1/2008 | Åkerstrom et al. | 340/612 |
| 7,458,260 B2 | 12/2008 | Roesner | 73/290 V |
| 2001/0015099 A1 | 8/2001 | Blaine | 73/290 R |
| 2003/0200801 A1 | 10/2003 | Lipscomb et al. | 73/290 V |
| 2004/0251919 A1 | 12/2004 | Stahlmann et al. | |
| 2006/0103393 A1* | 5/2006 | Stahlmann et al. | 324/658 |
| 2006/0201234 A1 | 9/2006 | Abe et al. | 73/53.01 |
| 2007/0110618 A1* | 5/2007 | Sasanuma et al. | 422/68.1 |

* cited by examiner

LIQUID LEVEL AND COMPOSITION SENSING SYSTEMS AND METHODS USING EMF WAVE PROPAGATION

CROSS-REFERENCE TO RELATED APPLICATIONS

This application is related to U.S. patent application Ser. No. 11/431,912, filed May 10, 2006, entitled System and Method for Sensing Liquid Levels Using EMF Wave Propagation; and U.S. Provisional Patent Application Ser. No. 60/875,439, filed Dec. 18, 2006, entitled Fuel Composition Sensing Systems and Methods Using EMF Wave Propagation, both of which are hereby incorporated herein by reference.

BACKGROUND OF THE INVENTION

1. Field of the Invention

This invention relates generally to systems and methods for sensing the condition of liquid in a tank or container. More particularly, embodiments of the present invention relate to sensing characteristics of automotive urea solution in a urea tank in a motor vehicle by propagating electromagnetic waves into a urea tank.

2. Description of the Prior Art

Selective Catalytic Reduction (SCR) vehicles, also referred to as Euro V vehicles, are diesel powered motor vehicles which are compatible with the use of an operating fluid to reduce emissions. Typically, the SCR vehicle has a urea tank, separate from the fuel tank, which is used to carry an operating fluid such as an automotive urea solution, or the like. Automotive Urea Solution (AUS) is a solution of high purity urea in de-mineralized water. AUS is stored in a urea tank of an SCR vehicle and is sprayed into the exhaust gases of the vehicle in order to convert oxides of nitrogen into elementary nitrogen and water. An SCR vehicle may then advantageously satisfy the Euro V Emissions Standard.

It is important for the Engine Management System (EMS) of an SCR vehicle to have information on the composition of the AUS, so that the EMS may adjust certain vehicle parameters to optimize vehicle performance, specifically emissions control.

In order to ensure this method of reducing emissions in an SCR vehicle remains effective, the quality of the AUS must be maintained. Contaminants, a change in the ratio of high purity urea to other constituents, temperature variation or other changes can impact the life expectancy of the AUS and the effectiveness of the AUS at reducing emissions.

SCR vehicles generally rely on the use of direct measurement systems to determine the level of AUS in a tank. Such systems typically comprise a plurality of sensors disposed at different levels along the vertical plane inside the urea tank. Such sensors typically have poor resolution, are intrusive, and do not detect the quality or temperature of the AUS. Such direct measurement systems also require installation of mechanisms inside the urea tank. Repair, replacement, or adjustment of such an internal direct measurement system is problematic. Furthermore, such systems are ineffective when employed in an SCR vehicle which is exposed to temperatures under minus eleven degrees centigrade, which is the temperature that AUS typically freezes, because such systems do not provide a means of measuring AUS temperature to enable the correct application of heat to prevent freezing of the AUS.

SCR vehicles generally rely on the use of indirect measurement systems to determine the effectiveness of the AUS in reducing vehicle emissions. Such indirect measurements are taken from the exhaust fumes and are passed to the EMS, whereupon the EMS may increase or reduce the quantity of AUS released from the tank. Such systems are typically slow to react and do not accurately reflect the actual quality or composition of the AUS.

Thus, the prior art fails to provide a reliable, inexpensive, and accurate system and method of measuring the level or quality of AUS in a motor vehicle urea tank, let alone both.

SUMMARY

The present invention is directed to systems and methods which accurately measure the level, temperature and/or quality of liquid, particularly AUS, in a motor vehicle by means of an internal or external AUS monitoring system. In particular, embodiments of the present invention may be used in SCR vehicles to detect certain characteristics of AUS including the amount of AUS in a urea tank and the percentage of ammonia content, and/or other constituents in the AUS. This information can be reported to the EMS or Body Control Module of the SCR vehicle, allowing the EMS to respond accordingly, thereby allowing adjustments to be made and improve, or at least, maintain the SCR vehicle emissions reduction performance, quickly and accurately. Embodiments of the present invention detect characteristics of the AUS without any direct contact with AUS, minimizing risk of leaks, or wear of the measuring device due to exposure to ammonia, or the like. To this end, embodiments of the present invention may, be deployed in conjunction with the urea tank at the bottom/side of a urea tank or internal to the urea tank.

Embodiments of the present invention may generate an RF signal of a variable frequency across a resonant circuit, which comprises an inductor and a PCB trace capacitor, capacitor plates, and/or the like. Electromagnetic radiation is propagated into the urea tank. The conductivity and dielectric properties of the AUS change the impedance of stated trace capacitor/capacitor plates and/or stated inductor. These changes are proportional to certain characteristics of the AUS including its level and/or the ammonia content of the AUS, and are preferably detected by a microcontroller, or the like, and then transmitted to the EMS. As such the present systems and methods provide a cost effective solution, well suited, not only for original equipment applications but also for up-fit or retro-fit. The present systems and methods are highly responsive and provide immediate information to the EMS, allowing adjustments to be made and improve/maintain the SCR vehicle emissions reduction performance, quickly and accurately. In various embodiments, auto-compensation may be provided so that the measured electrical parameter provides an accurate indication of the liquid level and composition in the tank, independent of variations in operating conditions, such as ambient temperature. The system can include a physical or wireless data interface to facilitate external transmission of the AUS measurement from the system to a central controller in the vehicle. The data can be transmitted periodically, in response to a change, by request from the central controller, or by request from an external device such as a diagnostic device.

Thus, in accordance with the present invention an embodiment of a method for liquid level and composition sensing using EMF wave propagation might include generating an RF signal at an operating frequency, coupling the RF signal to a resonant circuit, the resonant circuit having a resonant frequency and including an inductor positioned proximate to liquid in a tank and measuring a change in an electrical parameter associated with the resonant circuit caused by a variation in at least one property of the liquid proximate to the inductor. As noted, the liquid may be urea. The RF signal may be substantially sinusoidal and may have a constant frequency. The resonant circuit may be a series-resonant inductor, capacitor, resistor circuit or a parallel-resonant inductor, capacitor, resistor circuit. Preferably the inductor of the resonant circuit in placed in close proximity to the tank, causing electromagnetic radiation to propagate into a space defined within the tank, whereby the liquid in the tank acts as an electrical load to the series resonant circuit in a manner proportionate to the constituents of the liquid in the tank. The property of the liquid may be an electrical property and the measured change in the electrical parameter may be a function of a variation in the electrical property of the liquid. Where the liquid is an automotive urea solution, the variation in the property may be a function of liquid composition such as the ammonia concentration in the automotive urea solution or a function of the level of the automotive urea solution in the tank. The aforementioned measuring of a change in an electrical parameter associated with the resonant circuit may comprise measuring a change in voltage at the resonant circuit or a change in the resonant frequency of the resonant circuit. Preferably, the operating frequency of the RF signal may be calibrated to compensate for physical and/or electrical properties of the tank and such calibration may be carried out automatically. In particular, calibration of the operating frequency may include sweeping between a range of frequencies, from a first frequency to a second frequency, to identify the operating signal within the range and measuring a parameter of a resonant circuit from the operating frequency. The measured parameters may include the resonant frequency of the resonant circuit and/or the amplitude of the resonant frequency of the resonant circuit. Also, in accordance with the present invention the measured change I the liquid may be converted to a value representing a concentration of ammonia in the liquid and the measured change in the liquid may be transmitted to an external device Embodiments of a monitoring device of the present invention may include an antenna driver having output terminals, and input terminals, coupled to an RF generator; a resonant circuit coupled to the antenna driver and having an inductor positioned proximate a liquid in a container or tank; and a controller, including the RF generator, and controlling an operating frequency of the RF generator to be proximate to a resonant frequency of the resonant circuit and measuring a change in an electrical parameter associated with the resonant circuit caused by changes in the liquid in the tank. Again, the liquid may be an automotive urea solution and the changes in the liquid may include a change in level of the urea in the tank or a change in concentration of the urea, such as a change in ammonia concentration of the urea. The controller, antenna driver, and resonant circuit are mounted on a printed circuit board, which may be flexible and the sensor may be installed external to the container or tank. As noted, the resonant circuit includes a capacitor, which may be a printed circuit board trace capacitor.

An embodiment of a system for liquid level and composition sensing using EMF wave propagation might include an RF generator functional to generate an RF signal at an operating frequency; an antenna circuit electrically coupled to the RF generator, the antenna circuit comprising a resonant circuit and a radiating component mounted proximate to a urea tank, the resonant circuit having a resonant frequency; and a controller operatively connected to the RF generator and to the antenna circuit, the controller being functional to sweep between a range of a frequencies, from a first frequency to a second frequency, to identify a signal at the resonant frequency within the range and measuring a change in an electrical parameter of the signal associated with the resonant circuit caused by changes in a concentration of ammonia in urea in the tank. The controller may also transmit the measured change in the electrical parameter and/or the controller may convert the measured change in the electrical parameter to an ammonia concentration signal. Thus the controller may transmit the ammonia concentration signal to an engine management system of a selective catalytic reduction vehicle. As noted, the resonant circuit may be a series resonant circuit. In which case the controller may comprise a calibration module operative to sweep between a range of a frequencies, from a first frequency to a second frequency, to identify a signal at the resonant frequency within the range and measuring a change in an electrical parameter of the signal associated with the resonant circuit caused by changes in concentration of ammonia the urea in the tank. The controller might also include a compensation module functional to adjust the ammonia concentration signal for changes in ambient temperature or changes in temperature of the liquid in the tank.

The foregoing has outlined rather broadly the features and technical advantages of the present invention in order that the detailed description of the systems and methods that follow may be better understood. Additional features and advantages of the systems and methods will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The accompanying drawings, which are incorporated in and form part of the specification in which like numerals designate like parts, illustrate embodiments of the present invention and together with the description, serve to explain the principles of the invention. In the drawings.

DETAILED DESCRIPTION

The present systems and methods can determine the type of liquid in a container, particularly where the liquid is substantially water and is not limited to the examples used in this description. In the illustrated and described embodiments, the present system can provide this information to an automotive EMS, which may use the information to prevent improper operation of SCR vehicles with water or the like in the urea tank rather than the AUS recommended by the vehicle manufacturer, as well as to detect the level and or concentration of urea in a tank.

Figure 1:
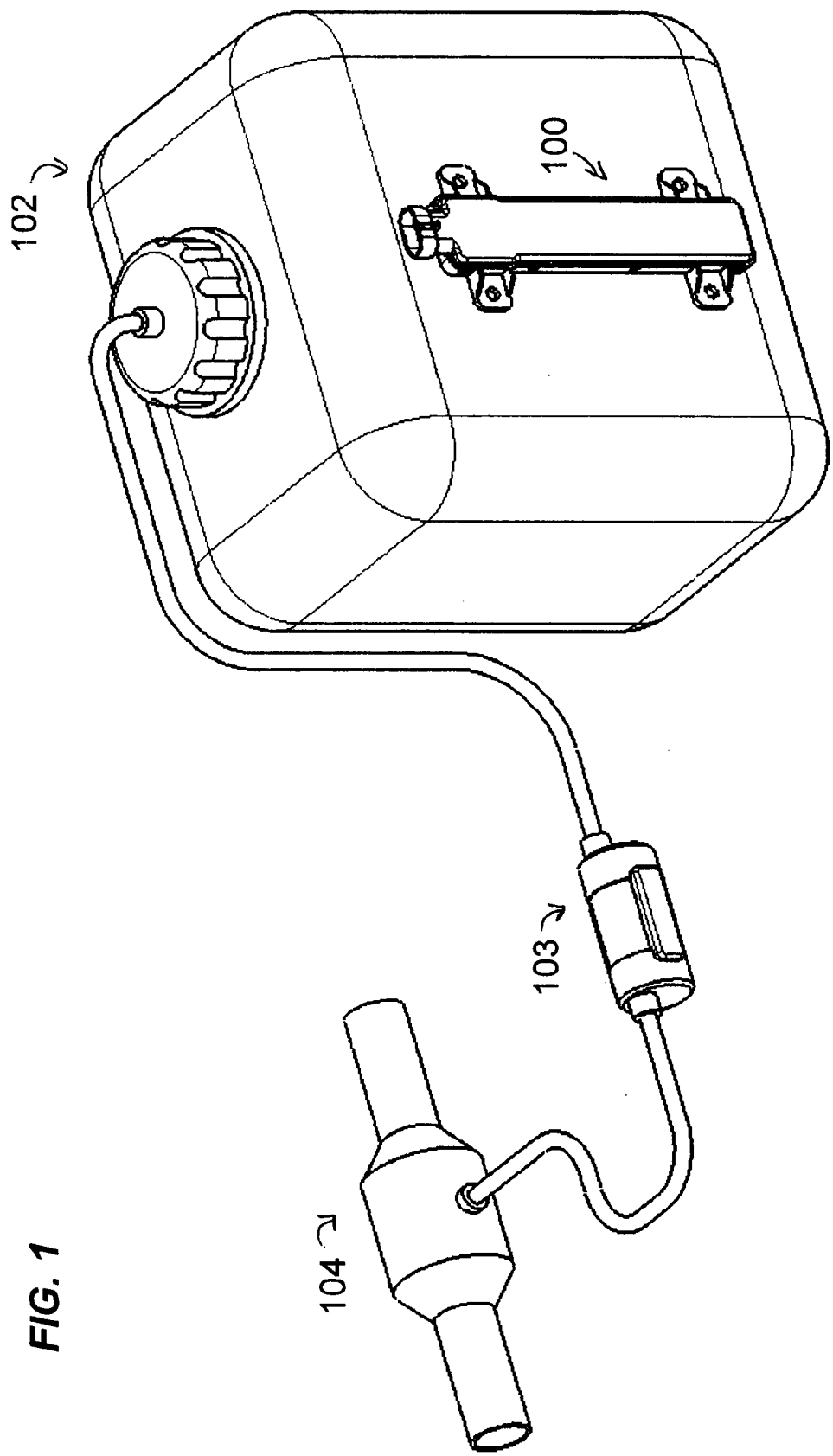
FIG. 1 is a perspective view of an external embodiment of an AUS system of the present invention deployed in conjunction with a urea tank.

FIG. 1 shows an embodiment of AUS monitoring device 100 of the present invention disposed in conjunction with urea tank 102, such as mounting the AUS monitoring device to the exterior of the tank. Various embodiments call for mounting the AUS monitoring device of the present invention to the exterior side or bottom of a tank. Urea tank 102 may be made from a non-conductive material such as plastic. AUS from urea tank 102 may be pumped by means of a pump 103 into exhaust 104 of a vehicle for emission control purposes.

Figure 2:
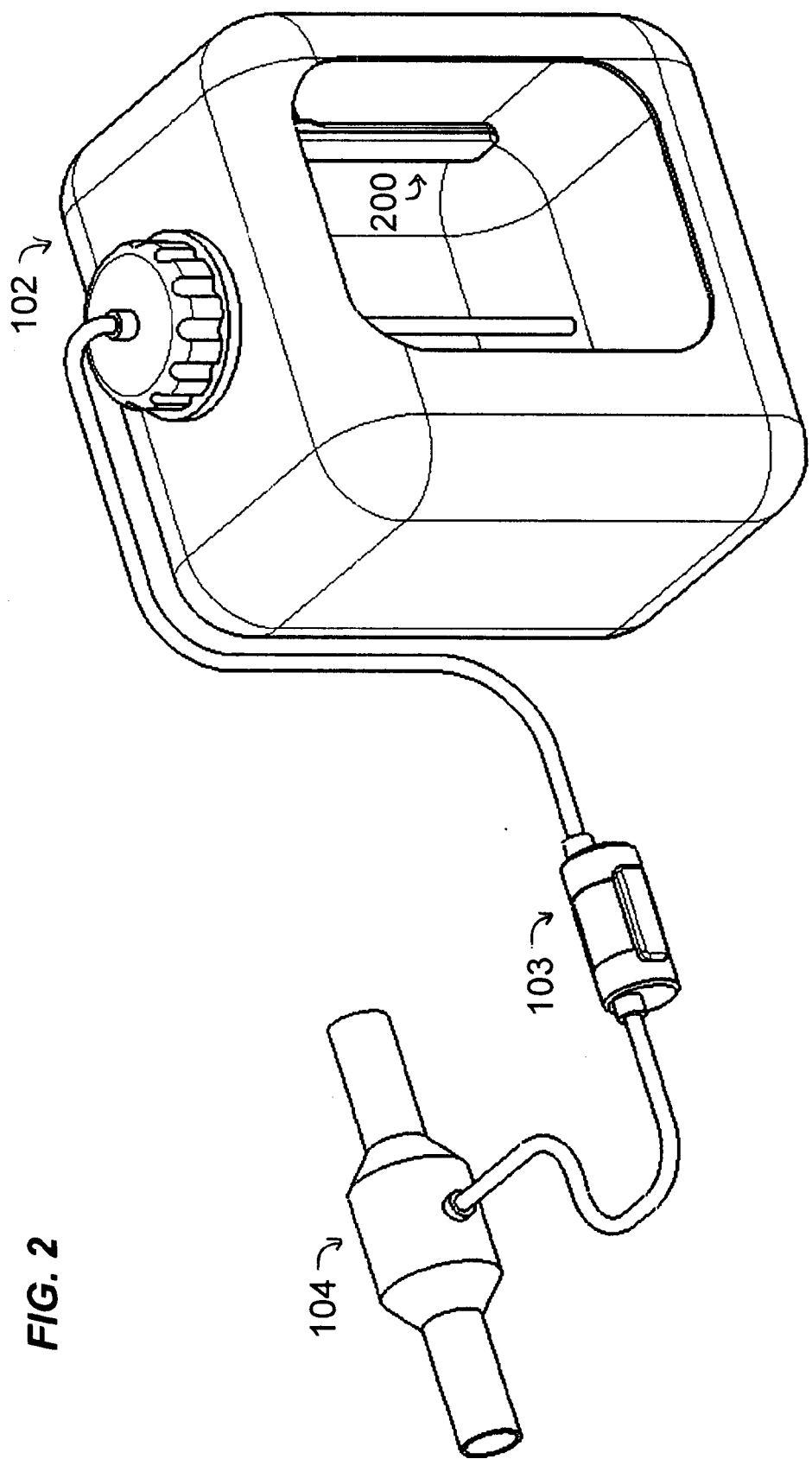
FIG. 2 is a partially fragmented perspective view of an internal embodiment of an AUS system of the present invention deployed in conjunction with a urea tank.

FIG. 2 shows another embodiment (200) of the AUS monitoring device of the present invention disposed in conjunction with urea tank 102, such as mounting the AUS monitoring device 200 to the interior of the tank. This embodiment may be of particular use where urea tank 102 is comprised of a conductive material, such as metal.

Figure 3:
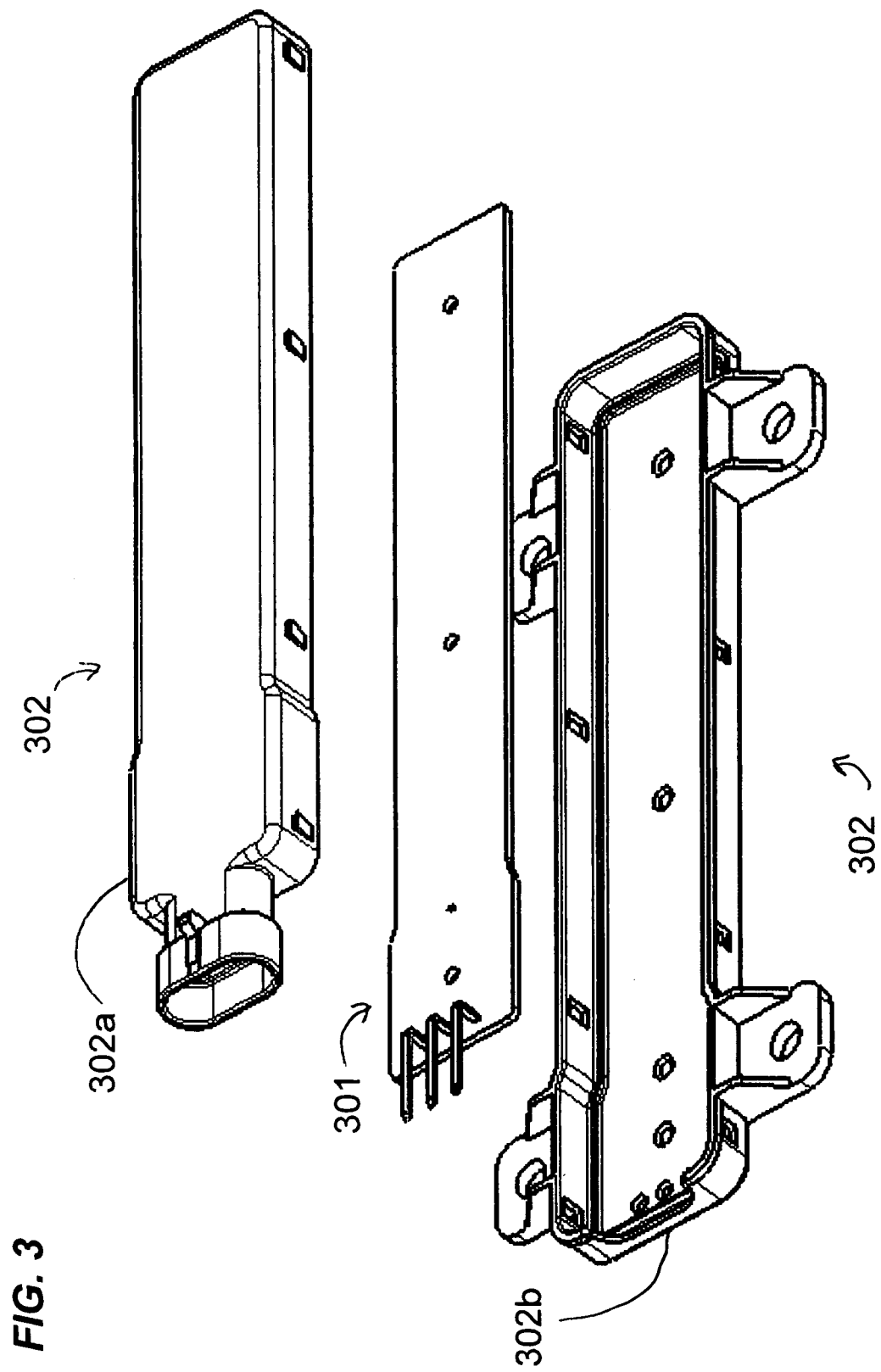
FIG. 3 is an exploded perspective view of the AUS monitoring device of FIG. 1.

FIG. 3 illustrates an embodiment of AUS monitoring device 100 or 200 including PCB 301 disposed in housing 302, shown as having two parts 302a and 302b. As discussed in greater detail with respect to FIG. 4 below, PCB 301 may mount and or define controller 401, the controller might include RF generator 402 and analog-to-digital converter 403 (ADC). PCB 301 might also include antenna circuitry 405 including antenna driver 406 having output terminals, and input terminals, coupled to the RF generator and resonant circuit 410. Resonant circuit 410 preferably includes inductor 411 and capacitor or PCB trace capacitor 412 positioned proximate a liquid in tank or container 102.

Figure 4:
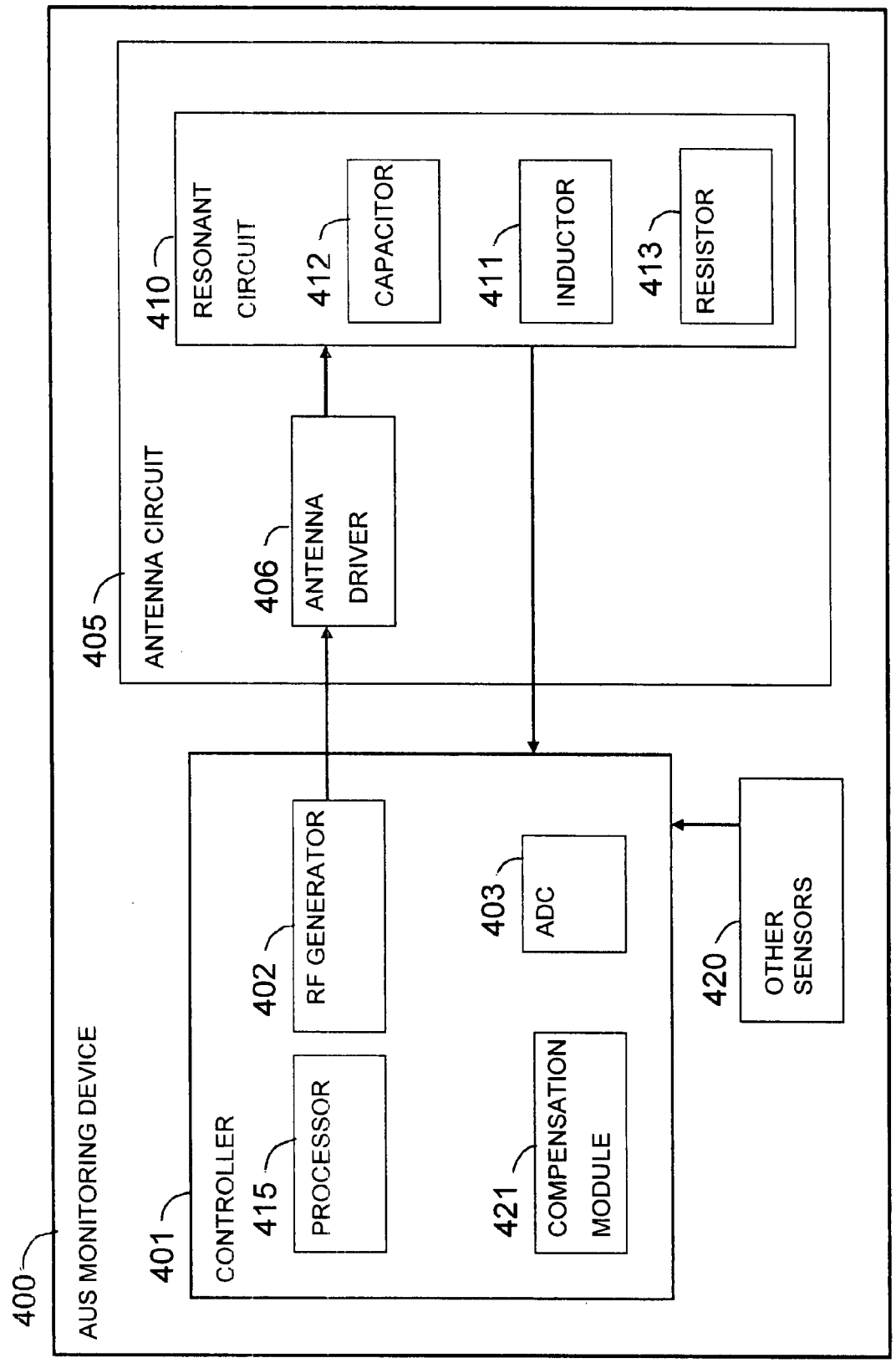
FIG. 4 is a block diagram view of certain functional elements within the AUS monitoring device of FIGS. 1, 2 and 3.

Embodiments of AUS monitoring devices 100 and 200 illustrated in FIGS. 1-3 may employ circuitry similar to circuitry 400 depicted in FIG. 4. Resonant circuit 410, which may be an LCR (inductor-capacitor-resistor) circuit, may be a series or parallel resonant circuit. Resonant circuit 410 preferably comprises resistor 413 as well as capacitor 421 and inductor 411 discussed above. Inductor 411 and/or capacitor 412 may be in discrete form, in PCB trace form, or otherwise formed. By placing inductor 411 of resonant circuit 410 in close proximity to tank 102, electromagnetic radiation may be propagated into liquid space 103 defined within tank 102. Whereby, the AUS, other liquid, and/or solids inside the tank acts as an electrical load on resonant circuit 410 in a manner proportionate to the level and/or the constituents of the liquid or the presence of solids in the tank. The conductivity and dielectric properties of the liquid change the impedance of discrete/trace capacitor 412 or discrete/trace inductor 411.

The present invention measures properties of a liquid, such as AUS. These properties are preferably electrical properties and a measured change in an electrical parameter of the liquid is a function of a variation in the electrical property of the liquid. Where the liquid is AUS, the variation in electrical property may be a function of the amount of the liquid present and the composition of the liquid. Measurements of electrical properties may include measuring a change in voltage at resonant circuit 410 and/or measuring a change in the resonant frequency of the resonant circuit, such as may be accomplished by analog to digital converter (ADC) 403.

Preferably, RF generator 402 generates an RF signal at an operating frequency and antenna circuit 405 is electrically coupled to RF generator 402. Also, resonant circuit 410 preferably has a frequency response curve centered around a resonant frequency. Controller 401 may be operatively connected to RF generator 402 and to antenna circuit 410 and may be functional to cause the operating frequency of RF generator 402 to be proximate to the resonant frequency of resonant circuit 410, and to measure a change in an electrical parameter associated with the resonant circuit caused by changes in the amount of AUS and/or the concentration and/or the ratio of ammonia in the AUS in tank 102 to other substances.

More particularly, in embodiments of the present systems and methods, a substantially sinusoidal RF signal of variable frequency is generated and coupled, employing antenna driver 406, to resonant circuit 410. Consequently, the liquid AUS inside tank 102 or 202 acts as an electrical load to resonant circuit 410 in a manner proportionate to the AUS level in urea tank 102 and/or certain characteristics of the AUS including the constituents and temperature of the AUS in urea tank 102. The loading effect of the AUS on resonant circuit 410 can cause a shift in the resonant frequency of the circuit, and/or a change in the amplitude of the signal from the circuit, and/or a change in the Q (quality factor) of the resonant circuit. In accordance with various embodiments of the present invention, the loading effect of the AUS is determined by monitoring a change in one or more electrical parameters associated with excited resonant circuit 410. For example, the voltage across resistor 413 in resonant circuit 410 may be monitored. Changes in this voltage may be detected and analyzed by controller 401 (processor 415), the EMS, or other circuitry associated with the SCR system, the results may be used to output a signal indicative of AUS composition, level or temperature. This output can be in the form of a digital or analog electrical signal.

Controller 401 or similar circuitry of AUS monitoring device 100 or 200 is preferably functional to transmit a measured change in an electrical parameter. In particular, controller 401 may be further functional to convert the measured change in the electrical parameter to an ammonia concentration and/or liquid level signal and to transmit this signal, or other information to an SCR vehicle EMS, or the like. The signal, and/or other information may be transmitted via a physical or wireless data interface to a central controller in the vehicle periodically, in response to a change, by request from controller 401, or by request from an external device such as a diagnostic device.

Preferably, the present invention allows for calibrating the operating frequency of the RF signal to compensate for physical and/or electrical properties of respective tank or container and external effects such as temperature. This calibration may be carried out by processor 415 or other circuitry when the tank is empty or full, or otherwise. For example, the calibration may be carried out automatically and/or periodically. The present systems and methods may employ calibration hardware and software that enable detection of a resonant frequency of resonant circuit 410 and the amplitude of that resonant frequency signal when the tank is empty. Alternatively or additionally, the present systems and methods may employ auto-calibration hardware and software that enable detection of the resonant frequency of resonant circuit 410 and the amplitude of the resonant frequency signal relative to previously known values. In particular embodiments, calibration might include sweeping to identify a resonant frequency signal in a range between a first frequency and a second frequency and measuring a parameter of the resonant circuit as the frequency of the RF signal is swept.

Various embodiments of the present invention detect the temperature of the AUS. In accordance with such embodiments the AUS monitoring device may include other sensors 420 for temperature or humidity, or other sensors. Controller 401 might also include compensation module 421 functional to adjust the liquid concentration signal for changes in temperature of the liquid, ambient temperature, and/or other measured or calculated parameters.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. For example, as noted, the present systems and methods can sense and measure the composition of liquid in other containers and/or transmission lines and are not limited to the examples used in this description. The system can be used in a wide variety of scientific, consumer, industrial, and medical environments. Accordingly, the appended claims are intended to include within their scope such processes, machines, manufacture, compositions of matter, means, methods, or steps.

What is claimed is:

1. A method comprising:
   generating an RF signal at an operating frequency;
   coupling the RF signal to a resonant circuit, the resonant circuit having a resonant frequency and including an inductor positioned proximate to urea in a tank;
   calibrating the operating frequency of the RF signal to compensate for physical and/or electrical properties of said tank;
   measuring a change in an electrical parameter associated with the resonant circuit caused by a variation in at least one property of the urea proximate to the inductor:
   determining a fluid level and at least one property of the urea based on the change in the electrical parameter associated with the resonant circuit; and
   transmitting the fluid level and at least one property of the urea to an external device.

2. The method of claim 1, wherein said RF signal is substantially sinusoidal and has a constant frequency.

3. The method of claim 1 wherein said resonant circuit is a series-resonant inductor, capacitor, resistor circuit.

4. The method of claim 1 wherein said resonant circuit is a parallel-resonant inductor, capacitor, resistor circuit.

5. The method of claim 1 further comprising placing an inductor of said resonant circuit in close proximity to said tank, causing electromagnetic radiation to propagate into a space defined within said tank, whereby the urea in said tank acts as an electrical load to said series resonant circuit in a manner proportionate to the constituents of said urea in said tank.

6. The method of claim 1 wherein the at least one property of the urea is an electrical property and the measured change in the electrical parameter is a function of a variation in the electrical property of the urea.

7. The method of claim 1 wherein the urea is an automotive urea solution and variation in said property is a function of urea composition.

8. The method of claim 1 wherein the urea is an automotive urea solution and the variation in said property is a function of the ammonia concentration in the automotive urea solution.

9. The method of claim 8, further comprising compensating said measured change or said at least one property of the liquid to adjust an ammonia concentration measurement for changes in ambient temperature.

10. The method of claim 8, further comprising compensating said measured change or said at least one property of the liquid to adjust an ammonia concentration measurement for changes in temperature of the liquid.

11. The method of claim 1 wherein the urea is a liquid automotive urea solution and the variation in said property is a function of the level of the automotive urea solution in said tank.

12. The method of claim 1, wherein said measuring comprises measuring a change in voltage at the resonant circuit.

13. The method of claim 1, wherein said measuring comprises measuring a change in the resonant frequency of the resonant circuit.

14. The method of claim 1, wherein the operating frequency is calibrated automatically.

15. The method of claim 14, wherein said calibrating the operating frequency comprises sweeping between a range of a frequencies, from a first frequency to a second frequency, to identify said operating signal within said range and measuring a parameter of a resonant circuit from said operating frequency.

16. The method of claim 15 wherein the measured parameter includes the resonant frequency of the resonant circuit.

17. The method of claim 15 wherein the measured parameter includes the amplitude of the resonant frequency of the resonant circuit.

18. The method of claim 1, further comprising convering the measured change to a value representing a concentration of ammonia in said urea.

19. The method of claim 1, wherein said at least one property of the urea comprises a change in concentration, and a change in level of the urea solution.

* * * * *